(12) United States Patent
Chong

(10) Patent No.: US 9,549,671 B2
(45) Date of Patent: Jan. 24, 2017

(54) OPTICAL COHERENCE TOMOGRAPHY SYSTEM WITH MULTIPLE SAMPLE PATHS

(71) Applicant: SANTEC CORPORATION, Komaki, Aichi (JP)

(72) Inventor: Changho Chong, Komaki (JP)

(73) Assignee: SANTEC CORPORATION, Komaki (JP)

(*) Notice: Subject to any disclaimer, the term of this patent is extended or adjusted under 35 U.S.C. 154(b) by 0 days.

(21) Appl. No.: 14/601,945

(22) Filed: Jan. 21, 2015

(65) Prior Publication Data

US 2015/0201833 A1  Jul. 23, 2015

Related U.S. Application Data

(60) Provisional application No. 61/929,617, filed on Jan. 21, 2014.

(51) Int. Cl.
 *A61B 3/10*   (2006.01)
 *A61B 3/14*   (2006.01)
 *G01B 9/02*   (2006.01)

(52) U.S. Cl.
 CPC .......... *A61B 3/102* (2013.01); *G01B 9/02004* (2013.01); *G01B 9/02019* (2013.01); *G01B 9/02021* (2013.01); *G01B 9/02028* (2013.01); *G01B 9/02091* (2013.01); *G01B 9/02017* (2013.01)

(58) Field of Classification Search
 CPC ....... A61B 3/102; A61B 3/117; A61B 3/1005; A61B 5/0066; G01B 9/02004; G01B 9/02044; G01B 9/02091; G01B 9/02057; G01B 9/02028; G01B 9/02017; G01B 9/02019; G01B 9/02021; G02B 13/0095; G02B 17/0896

USPC .......................................... 351/206, 205, 208
See application file for complete search history.

(56) References Cited

U.S. PATENT DOCUMENTS

| | | | | |
|---|---|---|---|---|
| 7,400,410 B2* | 7/2008 | Baker | ............... | A61B 3/1005 351/210 |
| 8,625,104 B2* | 1/2014 | Izatt | ............... | A61B 3/102 356/479 |
| 2005/0213103 A1* | 9/2005 | Everett | ............... | A61B 5/0066 356/479 |

(Continued)

OTHER PUBLICATIONS

Dai et al., "Optical coherence tomography for whole eye segment imaging," Optics Express, vol. 20, No. 6 (2012) pp. 6109-6115.

(Continued)

*Primary Examiner* — Bumsuk Won
*Assistant Examiner* — Collin X Beatty
(74) *Attorney, Agent, or Firm* — Foley & Lardner LLP

(57) ABSTRACT

Improved optical coherence tomography (OCT) imaging systems are generally described. In an example, an OCT imaging system includes a tunable laser source, an interferometer, a splitter, and a detector. The tunable laser source is configured to provide a wavelength-scanned beam. The interferometer is configured to split the wavelength-scanned beam into a reference beam and an object beam. The splitter is configured to split the object beam into a first path corresponding to an anterior chamber imaging component and a second path corresponding to a retinal imaging component. The detector is configured to detect a signal caused by interference between the reference beam and at least a portion of the object beam reflected from the eye.

20 Claims, 3 Drawing Sheets

(56) References Cited

U.S. PATENT DOCUMENTS

| | | |
|---|---|---|
| 2007/0076217 A1 | 4/2007 | Baker et al. |
| 2007/0291277 A1 | 12/2007 | Everett et al. |
| 2010/0284021 A1 | 11/2010 | Hacker |
| 2012/0026466 A1* | 2/2012 | Zhou .................... A61B 3/1015 351/214 |
| 2012/0188555 A1* | 7/2012 | Izatt ....................... A61B 3/102 356/479 |
| 2014/0111774 A1* | 4/2014 | Komine ................... A61B 3/14 351/221 |

OTHER PUBLICATIONS

Dhalla et al., "Simultaneous swept source optical coherence tomography of the anterior segment and retina using coherence revival," Optics Letters, vol. 37 No. 11, Jun. 1, 2012, pp. 1883-1885.
International Search Report and Written Opinion in PCT/IB2015/000808 dtd Oct. 20, 2015 (12 pages).
Jeong et al., Spectral-domain 1-13 OCT with dual illumination and interlaced detection for simultaneous anterior segment and retina imaging, Optics Express, vol. 20 No. 17, dtd Aug. 13, 2012, pp. 19148-19159.

* cited by examiner

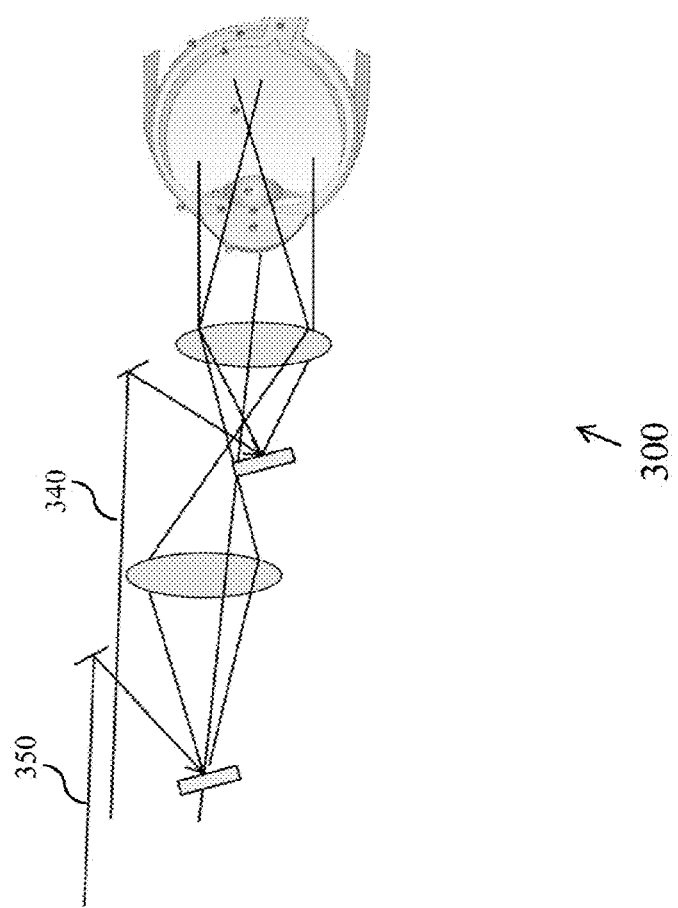

OPTICAL COHERENCE TOMOGRAPHY SYSTEM WITH MULTIPLE SAMPLE PATHS

CROSS-REFERENCE TO RELATED PATENT APPLICATIONS

This application claims priority from U.S. Provisional Application No. 61/929,617, filed Jan. 21, 2014, which is incorporated herein by reference in its entirety.

BACKGROUND

The following description is provided to assist the understanding of the reader. None of the information provided or references cited is admitted to be prior art.

Fourier domain optical coherence tomography (OCT) includes Spectral Domain OCT and Swept Source OCT. Swept source OCT is advantageous in deep imaging ranges because of the narrow line width of the laser, which enables higher coherence during rapid sweep. The majority of applications in ophthalmic OCT use swept source OCT, which is traditionally intended for either anterior chamber or retinal imaging. One can try to accommodate both anterior chamber and retinal imaging in a single integrated device. However different optical configurations are generally required for each. For anterior chamber imaging, the beam scan is perpendicular to the sample or corneal and with a focusing shallow. While for retina imaging, because of the presence of refraction by the eye itself, the beam scan has to be convergent with larger beam size to focusing deep or collimating. This generally requires either the adjustment of the focus beam and scanning pattern or having two arrangements in one system.

SUMMARY

The present technology provides an improved OCT imaging system that includes a tunable laser source, an interferometer, a splitter, and a detector. The tunable laser source is configured to provide a wavelength-scanned beam. The interferometer is configured to split the wavelength-scanned beam into a reference beam and an object beam. The splitter is configured to split the object beam into a first path corresponding to an anterior chamber imaging component and a second path corresponding to a retinal imaging component. The detector is configured to detect a signal caused by interference between the reference beam and at least a portion of the object beam reflected from the eye.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

FIG. 3 depicts an OCT system and/or device including multiple optical path lengths in accordance with still another illustrative embodiment.

DETAILED DESCRIPTION

Figure 1:
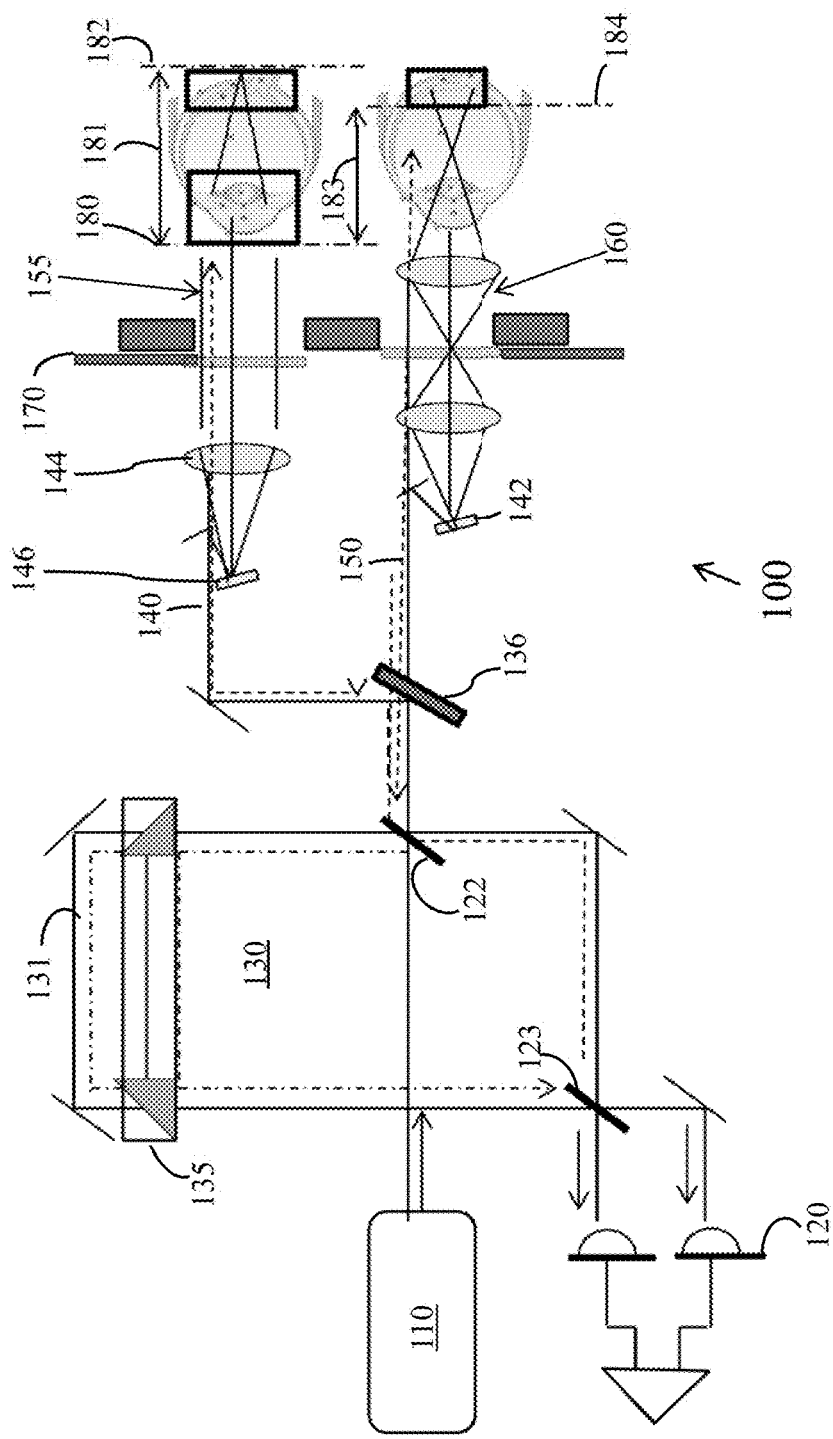
FIG. 1 depicts an OCT system and/or device including multiple optical path lengths in accordance with an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Described herein is an optical coherence tomography (OCT) device that includes a first light beam path for anterior chamber imaging and a second light beam path for retinal imaging within the same device.

FIG. 1 depicts an OCT system and/or device 100 including multiple optical path lengths in accordance with an illustrative embodiment. The OCT system 100 includes a wavelength scanning-type laser light source 110 or other suitable light source. In an embodiment, the light source 110 is configured to output a laser beam with a periodically modified wavelength. The output of the light source 110 is provided to an interferometer 130. The interferometer 130 includes various space type combining mirrors and half mirrors 122, 123. In the interferometer 130, a part of the light is reflected and applied as a reference light. The remaining light is emitted from the interferometer 130 and transmitted to a splitter/combiner mirror 136 that splits the emitted light into two distinct optical paths. A reflected light from the splitter/combiner mirror 136 is incident on the interferometer 130 creating an interference light that is incident on a balanced detector 120. In an embodiment, the balanced detector 120 converts the light signal into an electrical signal and the output is applied to a signal processing unit. In an embodiment, the signal processing unit is configured to generate a cross-sectional image by Fourier transform based on frequency change and intensity of the reflected light, and the image is displayed on an image display unit. In addition, a memory and a scan control unit may be connected to the signal processing unit.

The splitter/combiner mirror 136 splits the emitted light into two distinct optical paths that may be used for anterior chamber imaging (e.g., Sample path 140) and retinal imaging (e.g., Sample path 150), respectively. (In additional embodiments, the system may include additional splitters and more than two sample paths.) In an embodiment, the splitter/combiner mirror 136 splits the emitted light so that a majority of power is transmitted to the anterior chamber imaging components and the remaining minority of the power is transmitted to the retinal imaging components for the device/system. For example, in one implementation, 70 percent of the power is transmitted to the anterior chamber imaging components and 30 percent of the power is transmitted to the retinal imaging components for the device/system. Such an embodiment may be useful because laser exposure limits are often lower for retinal imaging and higher for anterior chamber or convergent beam imaging.

In an embodiment, for anterior chamber imaging, a single object lens 144 is used and a scan mirror 146 is placed at the back focal plane of the lens 144 to scan the focused beam in a perpendicular direction relative to the sample and a parallel direction relative to the optical axis. In another embodiment, for retinal imaging, a two lens system is used and is configured in a 4 f system so that the beam scan is convergent with respect to the sample and so that the beam scan spans the retinal area with a desired range.

The optical path length is adjusted to have an offset 183, which is equivalent to the optical length of an average human eye ball, for example, ~30 mm (20 mm×1.35 (n)) in an embodiment.

The OCT system 100 further includes two apertures: a first aperture 155 through which anterior chamber imaging is performed and a second aperture 160 through which retinal imaging is performed. In an embodiment, shutters 170 may be positioned to selectively close each aperture 155, 160, respectively. Accordingly, by sliding the position of an aperture from a first position to a second position in a direction perpendicular to the optical axis of eye, one can open or close the respective apertures and once can change the imaging range between anterior chamber imaging and retinal imaging. In an embodiment, the shutters 170 for each aperture may be combined so that movement of the shutter 170 opens one aperture and simultaneously closes another aperture (or vice versa). In another embodiment, if there is a path length switch 135 to change the path length of sample path 140 so that position O1 180 which is at a front side of the cornea goes to the backside of retina with predetermined length D11' 181, by measuring the position of cornea and retina in each area, you can calculate the axial length. If each distance of cornea and retina from O1 180, and O1' 182 is Xc and Xr respectively, then the axial length is D11'-Xc-Xr. Here D11' 181 can be set to larger than a maximum of typical axial length of a human eye.

Figure 2:
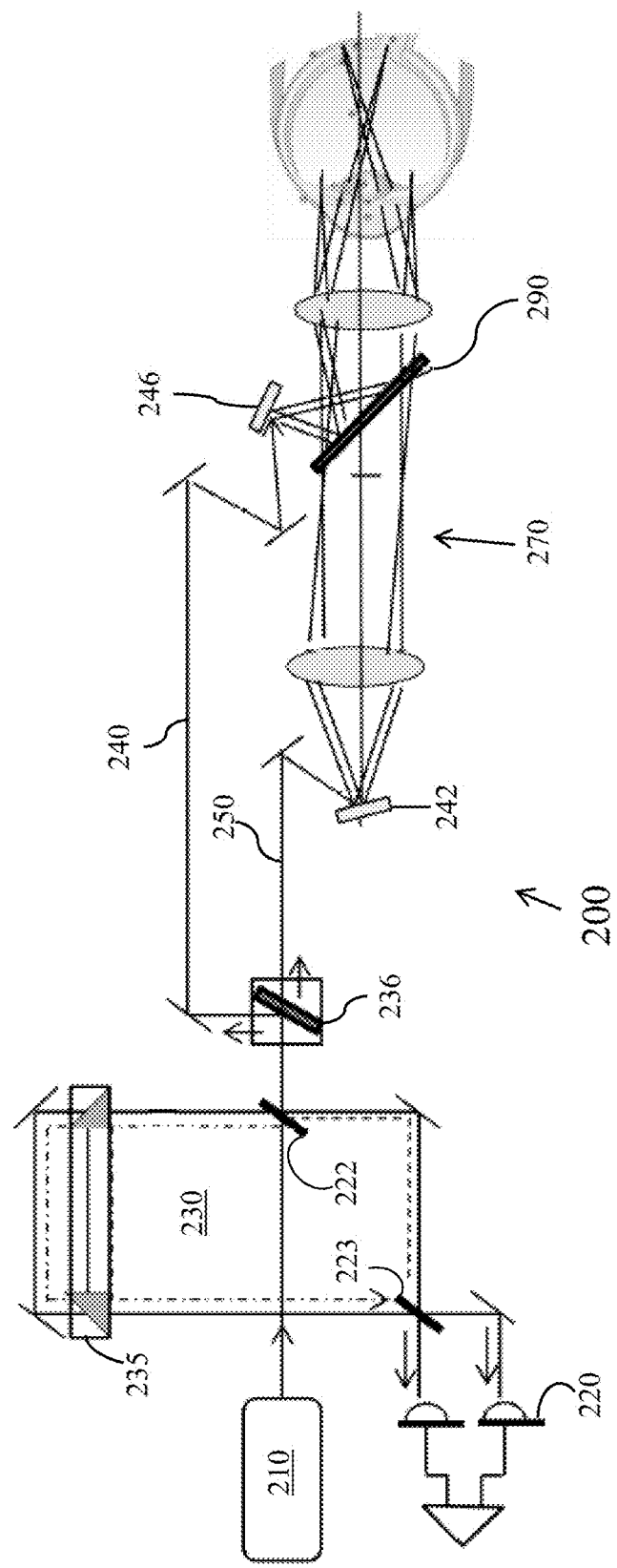
FIG. 2 depicts an OCT system and/or device including multiple optical path lengths in accordance with another illustrative embodiment.

FIG. 2 depicts an OCT system and/or device 200 including multiple optical path lengths in accordance with another illustrative embodiment. A 1×2 switch 236 splits the light emitted from the interferometer 230 into sample paths 240 and 250, respectively. In FIG. 2, sample paths 240 and 250 share a single common lens system 270. Sample path 250 routes light to a first end of the single common lens system 270 while a plurality of mirrors (or other components for routing light) introduces the beam of sample path 240 into the middle of the single common lens system.

Sample path 250 is configured with a scan mirror 242 positioned in the back focal plane of a two lens system with 4f configuration. Light beams pass through a splitter mirror 290 (e.g., a 7:3 splitter mirror) and after the second lens exits in a collimated beam in convergent scanning so that it scans the retinal area in a certain length after going through the eye lens system (cornea and crystalline lens). Light beams from sample path 240 are introduced into the second lens by having a partial reflecting mirror in between the lens and back focus. A scan mirror 246 for sample path 240 is positioned in the back focal plane of the second lens on the reflected path. In this way, the sample path 240 realizes beam focusing and scanning perpendicular to the anterior chamber position. The use of sample path 240 and 250 is switched by an optical switch between sample paths and interferometer 230.

FIG. 3 depicts an OCT system and/or device 300 including multiple optical path lengths 340, 350 in accordance with a third illustrative embodiment.

In an embodiment, the foregoing OCT systems/devices may be utilized with swept source OCT. Swept source OCT emits light that periodically changes wavelength over a certain range of wavelength. A light beam from a swept source (e.g., 110, 210) is divided into a sample path and a reference path. The light beam is projected onto the sample through the lens system with a scan mirror to laterally scan the position of the beam on a sample (e.g., an eye). The reflected light from the sample is recombined with the light passed through the reference path creating an interferometric signal. The interferometric signal is detected with a photodetector (e.g., balanced detector) (e.g., 120, 220). This detected light signal is converted to an electrical signal and digitized and Fourier-transformed to the signal of reflectivity along the depth direction inside the sample. This one-dimensional depth signal is repeatedly measured sequentially at neighboring positions by scanning the light beam and constructed into a two-dimensional signal for cross section imaging.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

The present disclosure is not to be limited in terms of the particular embodiments described in this application. Many modifications and variations can be made without departing from its spirit and scope, as will be apparent to those skilled in the art. Functionally equivalent methods and compositions within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can of course vary. It is also to be understood that the terminology used herein is for the purpose of describing particular embodiments only, and is not intended to be limiting.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims.

What is claimed is:

1. An optical coherence tomography (OCT) imaging system comprising:
   a tunable laser source configured to provide a wavelength-scanned beam;
   an interferometer configured to split the wavelength-scanned beam into a reference beam and an object beam;
   a splitter configured to split the object beam into a first path corresponding to an anterior chamber imaging component and a second path corresponding to a retinal imaging component, wherein the anterior chamber imaging component comprises a first scan mirror configured to image an anterior chamber of an eye, and wherein the retinal imaging component comprises a second scan mirror configured to image a retina of the eye; and
   a detector configured to detect a signal caused by interference between the reference beam and at least a portion of the object beam reflected from the eye.

2. The OCT imaging system of claim 1, further comprising a first aperture through which the portion of the object beam on the first path is configured to pass and a second aperture through which the portion of the object beam on the second path is configured to pass.

3. The OCT imaging system of claim 1, wherein the anterior imaging component further comprises a lens system optically coupled to the first scan mirror configured to image the anterior chamber.

4. The OCT imaging system of claim 1, wherein the retinal imaging component further comprises a lens system optically coupled to the second scan mirror configured to image the retina.

5. The OCT imaging system of claim 1, wherein the first path is distinct from the second path.

6. The OCT imaging system of claim 1, further comprising a processing unit configured to process a signal from the detector to generate an image.

7. The OCT imaging system of claim 1, wherein the first path comprises a lens system with a divergent beam and a lateral scanning pattern perpendicular to a sample, and wherein the second path comprises a lens system with a collimating beam and a divergent scanning pattern to the sample.

8. The OCT imaging system of claim 1, wherein a splitting ratio of the first path to the second path is greater than 50%.

9. The OCT imaging system of claim 1, wherein each of the first and second paths comprises a shutter configured to close over an aperture to switch between imaging ranges.

10. The OCT imaging system of claim 1, wherein a path length difference between the first path and the second path has an optical length equivalent to an axial length of an eye.

11. The OCT imaging system of claim 1, wherein first path is combined with the second path using a partially reflecting mirror inside the lens system of the second path.

12. The OCT imaging system of claim 1, wherein the first scan mirror is separate from the second scan mirror.

13. The OCT imaging system of claim 2, wherein the first path extends from the splitter to the first aperture, wherein the second path extends from the splitter to the second aperture, and wherein the first path is separate from the second path an entire distance between the splitter and the first aperture.

14. The OCT imaging system of claim 2, wherein the first path extends from the splitter to the first aperture, wherein the second path extends from the splitter to the second aperture, and wherein the first path is separate from the second path an entire distance between the splitter and the second aperture.

15. The OCT imaging system of claim 11, wherein the second path comprises a two lens system with 4f configuration and the beam of the first path is introduced to a second lens having the first scan mirror positioned in the back focus of the second lens.

16. The OCT imaging system of claim 11, wherein the second path comprises a two lens system with 4f configuration and the beam of the first path is introduced to a second lens having the second scan mirror positioned in the back focus of the second lens through a partial reflecting mirror.

17. A method comprising:
    emitting a wavelength-scanned beam from a tunable laser source;
    splitting, by an interferometer, the wavelength-scanned beam into a reference beam and an object beam;
    splitting, by a splitter, the object beam into a first path corresponding to an anterior chamber imaging component and a second path corresponding to a retinal imaging component, wherein the anterior chamber imaging component comprises a first scan mirror, and wherein the retinal imaging component comprises a second scan mirror configured to image a retina;
    imaging, by the first scan mirror, an anterior chamber of an eye;
    imaging, by the second scan mirror, a retina of the eye; and
    detecting, by a detector, a signal caused by interference between the reference beam and at least a portion of the object beam reflected from the eye.

18. The method of claim 17, further comprising passing a first portion of the object beam along the first path from the splitter to a first aperture through which the first portion of the object beam passes to the eye; and passing a second portion of the object beam along the second path from the splitter to a second aperture through which the second portion of the object beam passes to the eye.

19. The method of claim 18, wherein the first path is separate from the second path an entire distance between the splitter and the first aperture.

20. The method of claim 19, wherein the first path is separate from the second path an entire distance between the splitter and the second aperture.

* * * * *